United States Patent
Abe et al.

(10) Patent No.: US 8,399,022 B2
(45) Date of Patent: Mar. 19, 2013

(54) SPHERICAL FERRITE NANOPARTICLES AND METHOD FOR PRODUCING THE SAME

(75) Inventors: Masanori Abe, Meguro-ku (JP); Hiroshi Handa, Meguro-ku (JP); Takashi Nakagawa, Meguro-ku (JP); Masaru Tada, Meguro-ku (JP); Ryuichi Shimazu, Meguro-ku (JP); Toshiyuki Tanaka, Meguro-ku (JP)

(73) Assignees: Tokyo Institute of Technology, Tokyo (JP); Tamagawa Seiki Kabushiki Kaisha, Iida-shi (JP)

( * ) Notice: Subject to any disclaimer, the term of this patent is extended or adjusted under 35 U.S.C. 154(b) by 791 days.

(21) Appl. No.: 12/522,178

(22) PCT Filed: Dec. 28, 2007

(86) PCT No.: PCT/JP2007/075246
§ 371 (c)(1),
(2), (4) Date: Jul. 6, 2009

(87) PCT Pub. No.: WO2008/081917
PCT Pub. Date: Jul. 10, 2008

(65) Prior Publication Data
US 2010/0040553 A1    Feb. 18, 2010

(30) Foreign Application Priority Data
Jan. 5, 2007   (JP) .................... 2007-000649

(51) Int. Cl.
*A61K 9/14* (2006.01)
(52) U.S. Cl. ........................................ 424/489
(58) Field of Classification Search .......... None
See application file for complete search history.

(56) References Cited

U.S. PATENT DOCUMENTS

| | | | |
|---|---|---|---|
| 3,946,103 A | 3/1976 | Hund | |
| 4,675,251 A * | 6/1987 | Matijevic et al. | 428/404 |
| 4,837,046 A * | 6/1989 | Oishi et al. | 427/535 |
| 5,215,782 A * | 6/1993 | Yoshioka et al. | 427/132 |
| 6,793,842 B2 | 9/2004 | Akimoto et al. | |

FOREIGN PATENT DOCUMENTS

| | | |
|---|---|---|
| EP | 1 738 774 A1 | 1/2007 |
| JP | 1 246150 | 10/1989 |
| JP | 2 116631 | 5/1990 |
| JP | 2002 25816 | 1/2002 |
| JP | 2002 128523 | 5/2002 |
| JP | 2005 60221 | 3/2005 |
| JP | 2006 219353 | 8/2006 |
| JP | 2006 282582 | 10/2006 |
| JP | 2007 70195 | 3/2007 |

OTHER PUBLICATIONS

Tang, X. et al., "Preparation of M-Ba-ferrite fine powders by sugar-nitrates process", Journal of Materials Science, vol. 41, No. 12, p. 3867-3871, (2006).
Jiang, W. et al., "Preparation and properties of superparamagnetic nanoparticles with narrow size distribution and biocompatible", Journal of Magnetism and Magnetic Materials, vol. 283, No. 2-3, pp. 210-214, (2004).
Extended European Search Report issued Nov. 22, 2011, in Patent Application No. 07860449.3.
Youjin Lee, et al.,"Large-Scale Synthesis of Uniform and Crystalline Magnetite Nanoparticles Using Reverse Micelles as Nanoreactors under Reflux Conditions", Advanced Functional Materials, 15, No. 3, Mar. 2005, pp. 503-509.
Shougeng Sun, et al., "Size-Controlled Synthesis of Magnetite Nanoparticles", Journal of American Chemical Society, vol. 124, No. 28, 2002, pp. 8204-8205.
Yutaka Tamaura, et al., "The $Fe_3O_4$-Formation by the 'Ferrite Process': Oxidation of the Reactive $Fe(OH)_2$ Suspension Induced by Sucrose", Water Research, vol. 13, 1979, pp. 21-31.
Tadao Sugimoto, et al., Formation of Uniform Spherical Magnetite Particles by Crystallization from Ferrous Hydroxide Gels, Journal of Colloid and Interface Science, vol. 74, No. 1, Mar. 1980, pp. 227-243.
Ryuichi Shimzu, et al., "Control of Particle Size of Ferrite Nanoparticles by Seed Growth Method", Abstract of Spring Metting of Japan Soceity of Powder and Powder Metallurgy, 3-51A, 2006, p. 220.

* cited by examiner

*Primary Examiner* — Paul Dickinson
(74) *Attorney, Agent, or Firm* — Oblon, Spivak, McClelland, Maier & Neustadt, L.L.P.

(57) ABSTRACT

A method for producing spherical ferrite nanoparticles includes the steps of: preparing a first aqueous solution containing a disaccharide, an alkaline, an oxidation agent, seed particles and divalent iron ions; and conducting particle growth in the first aqueous solution to produce the spherical ferrite nanoparticles.

6 Claims, 7 Drawing Sheets

SUCROSE

FIG. 4B

CELLOBIOSE

FIG. 4C

MALTOSE

FIG. 4D

LACTOSE

FIG. 4E

TREHALOSE

FIG. 6A

CONCENTRATION OF 2.7mg/40ml
OF SEED PARTICLES

FIG. 6B

CONCENTRATION OF 13.5mg/40ml
OF SEED PARTICLES

US 8,399,022 B2

SPHERICAL FERRITE NANOPARTICLES AND METHOD FOR PRODUCING THE SAME

CROSS-REFERENCE TO RELATED APPLICATIONS

This application is based upon and claims the benefit of priority from the prior Japanese Patent Application No. 2007-000649 filed on Jan. 5, 2007; the entire contents which are incorporated herein by reference.

BACKGROUND

1. Field of the Invention

The present invention relates to spherical ferrite nanoparticles and a method for producing the spherical ferrite nanoparticles. The spherical ferrite nanoparticles are configured such that the sizes of the spherical ferrite nanoparticles are set almost equal to one another. The producing method is carried out in an aqueous water solution.

2. Background of the Invention

Ferrite particles dispersed in an aqueous solution can be employed for various uses and in various fields. Among the various uses and fields, the ferrite particles often and intensely applied for biotechnology or medical care so that various advanced requirements are imposed on the ferrite particles.

As the ferrite particles for biotechnology and medical care, such ferrite particles as having respective spherical shapes and respective sizes within a range of several ten nm through several hundred nm are required. Moreover, the size distribution in the ferrite particles is required to be narrowed so that the sizes of the ferrite particles are set almost equal to one another.

Since the size distribution in the ferrite particles is set in the order of several ten nm, the ferrite particles can pass through various portions of a living body. If the ferrite particles have respective polyhedral crystalline shapes, the ferrite particles can not be always modified uniformly by biological molecules or polymeric molecules because the property of each of the ferrite particles becomes different dependent on the kind of crystal plane of the polyhedral crystalline shape thereof. However, if the ferrite particles have respective spherical crystalline shapes, the ferrite particles can be modified uniformly so that each of the ferrite particles can be surface-modified uniformly by biological molecules or polymeric molecules. Moreover, if the ferrite particles are only crystalline particles, the ferrite particles may be adhered with one another at the crystal planes thereof or crystal sides thereof because the ferrite particles have respective crystal planes, thereby causing the aggregation of the ferrite particles easily. As described above, however, if the ferrite particles have respective spherical crystalline shapes, the ferrite particles are not likely to be aggregated and thus separated easily, thereby enhancing the dispersion of the ferrite particles in an aqueous solution.

Since the biochemical substance is normally operated in an aqueous solution, the ferrite particles to be modified with biological molecules or polymeric molecules are particularly required to be suitable for the dispersion in the aqueous solution. In this point of view, the surface property of each of the ferrite particles is desired to be suitable for the dispersion in the aqueous solution while each of the ferrite particles has its spherical shape.

If the ferrite particles with a uniform size are sufficiently dispersed in an aqueous solution, the thus obtained dispersion liquid can be introduced into a living body such that the dispersed ferrite particles can be moved smoothly in the living body.

The ferrite particles, which are easily dispersed in an aqueous solution, with a uniform particle size of several ten nm through hundred nm and respective spherical shapes as mentioned above are desired as magnetic particles suitable for the application in various biochemical fields and medical care fields. However, a producing technique for producing the magnetic particles has not yet established.

As of now, various synthetic methods capable of producing a large amount of ferrite nanoparticles has been developed. For example, raw material powders are mixed, fired and mechanically crushed to form the ferrite nanoparticles. However, such a producing method has an advantage of excellent productivity but has a disadvantage of nonuniform particle shape and size distribution. Moreover, it is proposed that a metallic raw material is evaporated in inert gas atmosphere so as to form the metallic nanoparticles through the cooling and aggregation of the metallic raw material by the collision with the inert gas and thus form the intended ferrite nanoparticles synthesized through the oxidation under low pressure oxidation atmosphere. Such a producing method is called as "metallic evaporation oxidizing method". According to the metallic evaporation oxidizing method, the intended ferrite nanoparticles can be shaped spherical but cannot be rendered uniform in particle size. The ferrite nanoparticles synthesized by the metallic evaporation oxidizing method are commercially available as "NanoTekR" made by C.I Kasei Co., Ltd. Furthermore, it is proposed that a raw material solution is splayed and the thus obtained mists are passed through high temperature area to be dried and synthesized, thereby forming the intended ferrite nanoparticles. Such a producing method is called as "splaying method" (Reference 1: JP-A 2002-025816). However, the splaying method has an advantage of capable of forming spherical ferrite nanoparticles but a disadvantage of large particle size distribution.

In this point of view, polyol method (Reference 2: B. Y. Lee, et al., Adv. Funct. Mater. 15 (2005)503.) and reverse micelle method (Reference 3: S. Sun and H. Zeng, J. Am. Chem. Soc. 124 (2002)8204.) are proposed. In these methods, the intended ferrite nanoparticles are synthesized in an organic solvent. According to these methods, the spherical ferrite nanoparticles with narrow particle size distribution can be synthesized, but the particles sizes of the spherical ferrite nanoparticles cannot be set to 16 nm or more and the spherical ferrite nanoparticles are covered with a surface-active agent. Since the surface-active agent is hydrophobicity, the spherical ferrite nanoparticles can be dispersed in an organic solvent, but cannot in an aqueous solution. In addition, if the ferrite nanoparticles are covered with the surface-active agent, it is difficult to immobilize biological molecules or polymeric molecules on the surfaces of the ferrite nanoparticles.

In view of the application of various biochemical fields and medical care fields, the ferrite particles easily dispersible in an aqueous solution are desired. Therefore, it is desired that the ferrite particles are synthesized in an aqueous solution.

As such a pioneer producing method as mentioned above, Reference 4 (Tamaura, et al.) and Reference 5 (Sugimoto et al.) can be exemplified. In Reference 4, the spherical ferrite particles can be obtained as part of water treatment process using the process that can precipitate ferrites from an aqueous solution. Concretely, $FeSO_4$ and a small amount of sucrose are added into a deoxidized pure water and then NaOH is added into the deoxidized pure water. Then, the deoxidized pure water is heated and the thus obtained hydroxides are contacted with a CO$_2$-removed air to form ferrite particles with a particle size within a range of 36 nm to 250 nm. In Reference 4, however, the size distribution of the ferrite particles becomes large. The inventors in this application surveyed Reference 4 so that the experimental results support the above-described results. Namely, the shapes of the ferrite particles can be made spherically but becomes random. Moreover, the particle size distribution in the ferrite particles becomes relatively large.

In Reference 5, the research about the particle configuration in the generation of iron oxides from hydroxide gels is described. Concretely, spherical ferrite particles within a particle size range of 30 nm to 1.1 μm can be obtained by generating the iron oxides from the hydroxide gel. In Reference 5, however, as shown in FIG. 7 of Reference 5, the particle sizes of the ferrite particles become almost uniform in the order of micro-meter, but not uniform in the order of less than 300 nm. Namely, the particle size distribution in the ferrite particles becomes relatively large in the order of less than 300 nm.

Accordingly, it is intensely desired to establish the producing method that can make the shapes of the ferrite particles spherical and can enhance the dispersion of the ferrite particles in an aqueous solution so that the ferrite particles can be suitable for biotechnology field and medical care field because as of now, such a producing method has not yet been established.

[Reference 1] JP-A 2002-025816

[Reference 2] B. Y. Lee, C. J. Bae, J. G. Park, H. J. Noh, J. H. Park and T. Hyeon, "Large-Scale Synthesis of Uniform and Crystalline Magnetite Nanoparticles Using Reverse Micelles as Nanoreactors under Reflux Conditions", Adv. Funct. Mater. 15(3), pp. 503-509, (2005)

[Reference 3] S. Sun and H. Zeng, "Size-Controlled Synthesis of Magnetite Nanoparticles", J. Am. Chem. Soc. 124, pp. 8204-8205 (2002)

[Reference 4] Y. Tamaura, G. S. Chyo and T. Katsura, "The Fe$_3$O$_4$-formation by the "ferrite process": Oxydation of the reactive Fe(OH)$_2$ suspension induced by sucrose", Water research 13(1), pp. 21-31 (1979)

[Reference 5] T. Sugimoto and E. Matijevic, "Formation of Uniform Spherical Magnetite Particles by Crystallization from Ferrous Hydroxide Gels", J. Colloidal and interface Science, 24(1), pp. 227-243(1980)

[Reference 6] JP-A 2006-219353

[Reference 7] Shimazu, Tada, Abe, Handa, "Control of Particle Size of Ferrite Nanoparticles by Seed Growth Method", Extended Abstract of Japan Society of Powder Metallurgy Meeting, Heisei 18, Spring, 3-51A (2006)

BRIEF SUMMARY OF THE INVENTION

In view of the above-described problems, it is an object to provide a new method for producing spherical ferrite nanoparticles with a uniform particle size within a range of 30 nm to 250 nm that is undeveloped as of now.

This invention relates to a method for producing spherical ferrite nanoparticles, including the steps of: preparing a first aqueous solution containing a disaccharide, an alkaline, an oxidation agent, seed particles and divalent iron ions; and conducting particle growth in the first aqueous solution to produce the spherical ferrite nanoparticles. The first aqueous solution is prepared by adding the seed particles and the divalent iron ions into a second aqueous solution containing the disaccharide, the alkaline and the oxidation agent.

The first aqueous solution is prepared by adding the alkaline and the seed particles into a third aqueous solution containing the divalent iron ions and the disaccharide to form a fourth aqueous solution and adding the oxidation agent into the fourth aqueous solution.

According to the producing method as described above, the intended spherical ferrite nanoparticles with a uniform particle size within a range of 30 nm to 250 nm and with a narrow particle size distribution can be synthesized. In this case, the dispersion of the ferrite nanoparticles in a water is excellent. Since the cohesive force between the adjacent ferrite nanoparticles is small in a water, the ferrite nanoparticles can be easily separated from one another by agitation and thus dispersed in the water even though the ferrite nanoparticles are settled. The reason may be originated from that since the ferrite nanoparticles are shaped spherically, the ferrite nanoparticles are not aggregated at the surfaces and sides thereof and the cohesive force between the adjacent ferrite nanoparticles may be weakened on the action of the disaccharides remaining on the surfaces of the ferrite nanoparticles.

The divalent iron ions can be supplied by adding a metallic salt containing the divalent iron ions such as FeCl$_2$ or FeSO$_4$.

The disaccharide is a compound made by glycoside coupling two monosaccharides one another. As a normal disaccharide, a sucrose (α-D-glucopyranosyl-β-D-fructofuranoside), cellobiose(4-o-(β-D-glucopyranosyl)-D-glucopyranose), trehalose (α-D-glucopyranosyl-α-D-glucopyranoside), maltose (4-o-(α-D-glucopyranosyl)-D-glucopyranose) and lactose (4-o-(β-D-galactopyranosyl)-D-glucopyranose) may be exemplified.

In the producing method of the spherical ferrite nanoparticles, trivalent iron ions may be contained.

It is desired that the concentration of the disaccharide in the first aqueous solution is set within a range of 0.1M to 5M and the ratio of the concentration of the divalent iron ions to the concentration of the disaccharide is set within a range of 0.002 to 50. If the concentration of the disaccharide is lower than the above-mentioned range, the ferrite nanoparticles are unlikely to be shaped spherically and respective large crystal planes. Particularly, it is desired that the concentration of the disaccharide is set to 0.2M or more and the ratio of the concentration of the divalent iron ions to the concentration of the disaccharide is set to 0.004 or more. If the concentration of the disaccharide is larger than the above-mentioned range, the ferrite nanoparticles may not be produced. Particularly, it is desired that the concentration of the disaccharide is set to 3M or less and the ratio of the concentration of the divalent iron ions to the concentration of the disaccharide is set to 30 or less.

As the oxidation agent, at least one selected from the group consisting of a nitric acid, a nitrous acid, a nitrate and a nitrite may be preferably employed. Since such an oxidation agent has a moderate oxidizing properties, the oxidation agent is suitable for the synthesis of the ferrite nanoparticles according to the producing method. As the nitrate, a sodium nitrate and a potassium nitrate may be exemplified. As the nitrite, a sodium nitrite and a potassium nitride may be exemplified.

The spherical ferrite nanoparticles according to the present invention can be produced by the producing method as described above.

The spherical ferrite nanoparticles have a number-averaged particle size within a range of 30 nm to 250 nm, and thus, the ratio of the spherical ferrite nanoparticles falling within a range of ±40% for the number-averaged particle size are 95% or more for all of the spherical ferrite nanoparticles. The surfaces of the ferrite nanoparticles may exhibit hydrophilicity.

The ferrite nanoparticles of the present invention are shaped spherically and produced in the order of nano-meter size (30 nm to 250 nm) so as to exhibit specific properties. The sphericity of each of the ferrite nanoparticles may be defined as follows. Supposed that the maximum size of the surface crystal plane of each ferrite nanoparticle is designated by the reference character "d" and the diameter of each ferrite nanoparticle is designated by the reference character "D", the sphericity can be defined by the ratio D/d of 5 or more. Moreover, since the ferrite nanoparticles can be generally observed by a transmission electron microscope, the sphericity can be defined by a roundness $\Delta r$ on the transmission electron microscope image. In this case, the roundness $\Delta r$ means the shift of the ferrite nanoparticle on the transmission electron microscope image from the ideal geometrical circle. Concretely, the roundness $\Delta r$ can be represented by the difference in radius between two concentric circles with the respective different radii $r_2$, $r_1$, that is, $\Delta r = r_2 - r_1$ when the outline of the transmission electron microscope image of each ferrite manoparticle is sandwiched by the two concentric circles with the radii $r_2$, $r_1$. With the use of the roundness $\Delta r$, the sphericity of each ferrite nanoparticle can be defined by the ratio $\Delta r/r_m$ of 0.3 or less. Here, "$r_m$" means an average diameter and then is represented by $r_m = (r_2 + r_1)/2$.

The surface-modified ferrite nanoparticles of the present invention includes the spherical ferrite nanoparticles produced through a particle growth in an aqueous solution containing a disaccharide, an alkaline, an oxidation agent, seed particles and divalent iron ions, and at least one surface modification agent selected from the group consisting of a surface-active agent, a hydroxyl acid and a sugar alcohol, the at least one surface modification agent modifying surfaces of the spherical ferrite nanoparticles. In this case, the dispersion of the ferrite nanoparticle modified in surface can be enhanced.

The spherical ferrite nanoparticles and the surface-modified ferrite nanoparticles may be covered with a surface covering agent. The thus obtained composite ferrite nanoparticles may be employed for various uses. As the surface covering agent, a polystyrene, a polyethylene, a polyacrylic acid ester, a polymethacrylic acid ester, a polyethylene glycol (PEG), a polyglycidyl methacrylate, a silica, and silane coupling agent may be exemplified.

The functional ferrite nanoparticles of the present invention includes the spherical ferrite nanoparticles, the surface-modified ferrite particles or composite ferrite nanoparticles; linker molecules coupled with surfaces of the spherical ferrite nanoparticles; probe molecules coupled with the linker molecules and capable of being specifically coupled with a substance to be examined.

The functional ferrite nanoparticles function as a test regent for recognizing, analyzing or screening at least one selected from the group consisting of a medical agent, an antigenic agent, an antibody, a receptor, a hapten, an enzyme, a protein, a peptide, a nucleic acid, a hormone, a saccharide, a pathogen and a toxin.

The functional ferrite nanoparticles are employed for detecting at least one selected from the group consisting of a diagnostic agent, a cell marking agent, an enzyme-immobilizing agent and a protein-refining agent.

The functional ferrite nanoparticles are employed as at least one selected from the group consisting of a magnetic hyperthermia heating element, an MRI contrast medium and a medical agent transferring carrier.

The functional ferrite nanoparticles are employed for a diagnostic method to detect a magnetization by a magnetic detector such as a SQUID (superconducting quantum interface device), a Hall sensor or a GMR (giant magneto-resistance effective) sensor.

The functional ferrite nanoparticles are employed for chromatography.

The functional ferrite nanoparticles are employed for at least one selected from the group consisting of soil improvement, water purification and air purification.

The functional ferrite nanoparticles are employed as at least one of an absorbing agent and a sensor.

Since the ferrite nanoparticles produced according to the present invention are shaped spherically so as not to have plane surfaces and to have a uniform particle size, the ferrite nanoparticles are suitable for various uses in addition to various biochemical applications and medical care applications. Moreover, since the ferrite nanoparticle can be easily surface-modified and easily separated from one another because the ferrite nanoparicles are unlikely to be adhered with one another at the crystal planes and sides thereof, the dispersion of the ferrite nanoparticles is excellent. Therefore, the ferrite nanoparticles can be passed through a minute flow path so as to be suitable for a MEMS, a body injection, a magnetic fluid and the like.

EXPLANATION OF SYMBOLS

102 . . . Step for dissolving disaccharide into $O_2$-removed pure water prepared through the bubbling of $N_2$ gas, 104 . . . Step for adding divalent iron ions as raw material of spherical ferrite nanoparticles into solution, 106 . . . Step for adding minute seed particles, 108 . . . Step for adding alkaline, 110 . . . Step for adding oxidation agent, 112 . . . Step for conducting reaction in container, 114 . . . Step for washing and magnetically separating, 116 . . . Ferrite nanoparticles, 302 . . . Step for dissolving disaccharide into pure water, 304 . . . Step for adding alkaline, 306 . . . Step for adding oxidation agent, 308 . . . Step for deoxidizing treatment, 310 . . . Step for heating, 312 . . . Step for adding seed particles, 314 . . . Step for adding divalent iron ions, 316 . . . Step for conducting particle growth, 318 . . . Step for washing and magnetically separating, 320 . . . Spherical ferrite nanoparticles

BEST MODE FOR IMPLEMENTING THE INVENTION

Hereinafter, the present invention will be described in detail with reference to the drawings.

Figure 1:
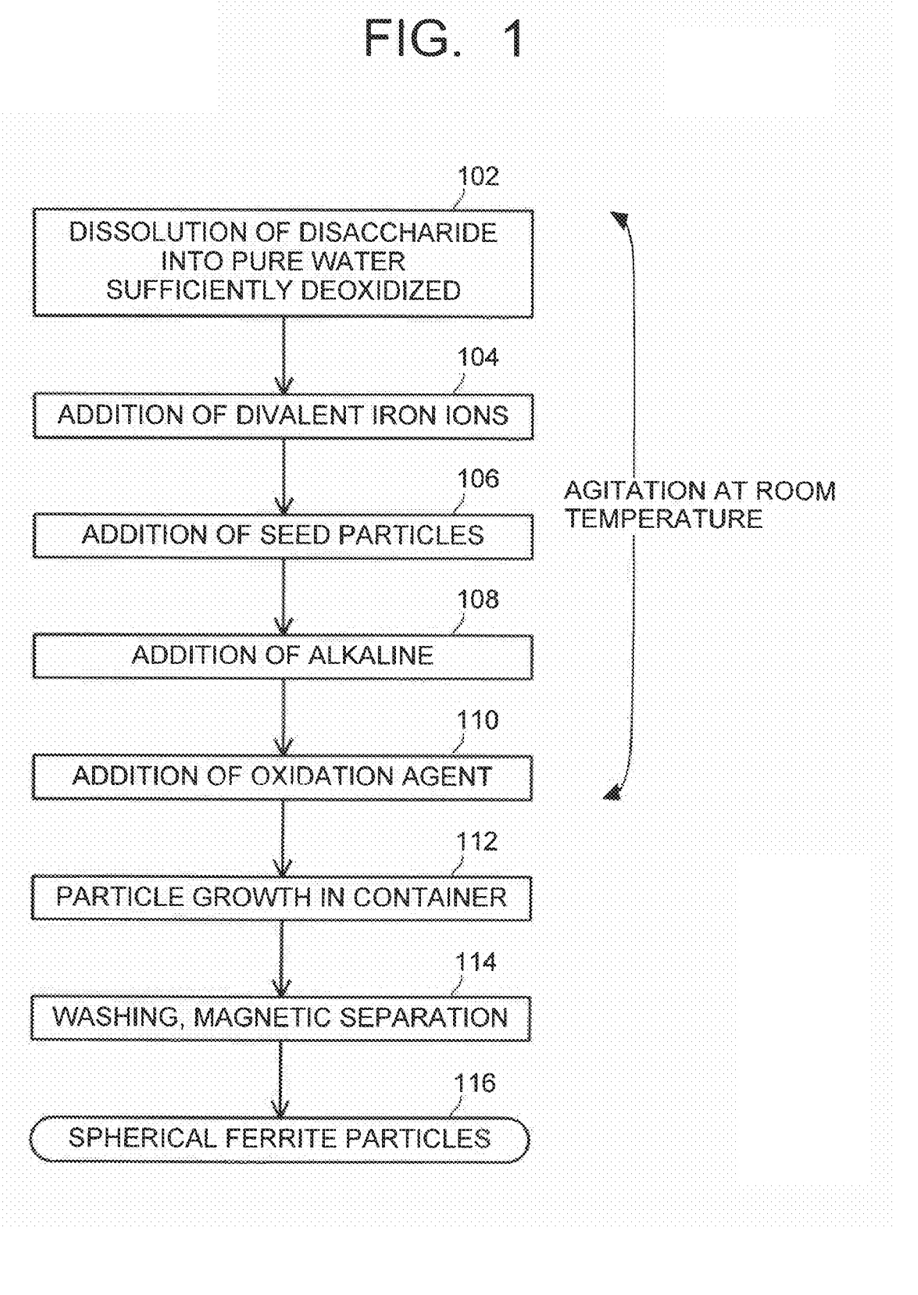
FIG. 1 is a flowchart showing the steps in the producing method according to an embodiment of the present invention.
Figure 2:
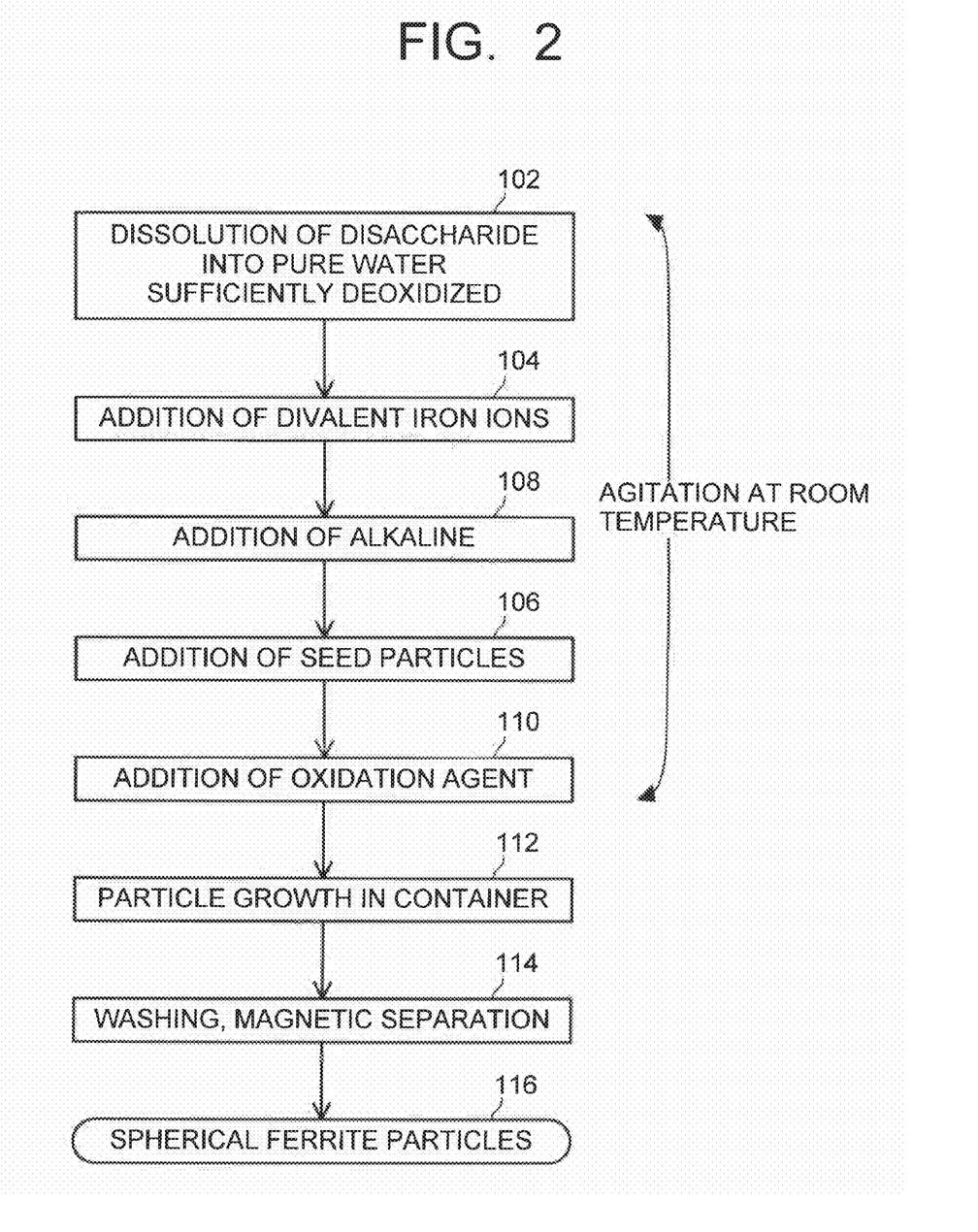
FIG. 2 is also a flowchart showing the steps in the producing method according to another embodiment of the present invention.
Figure 3:
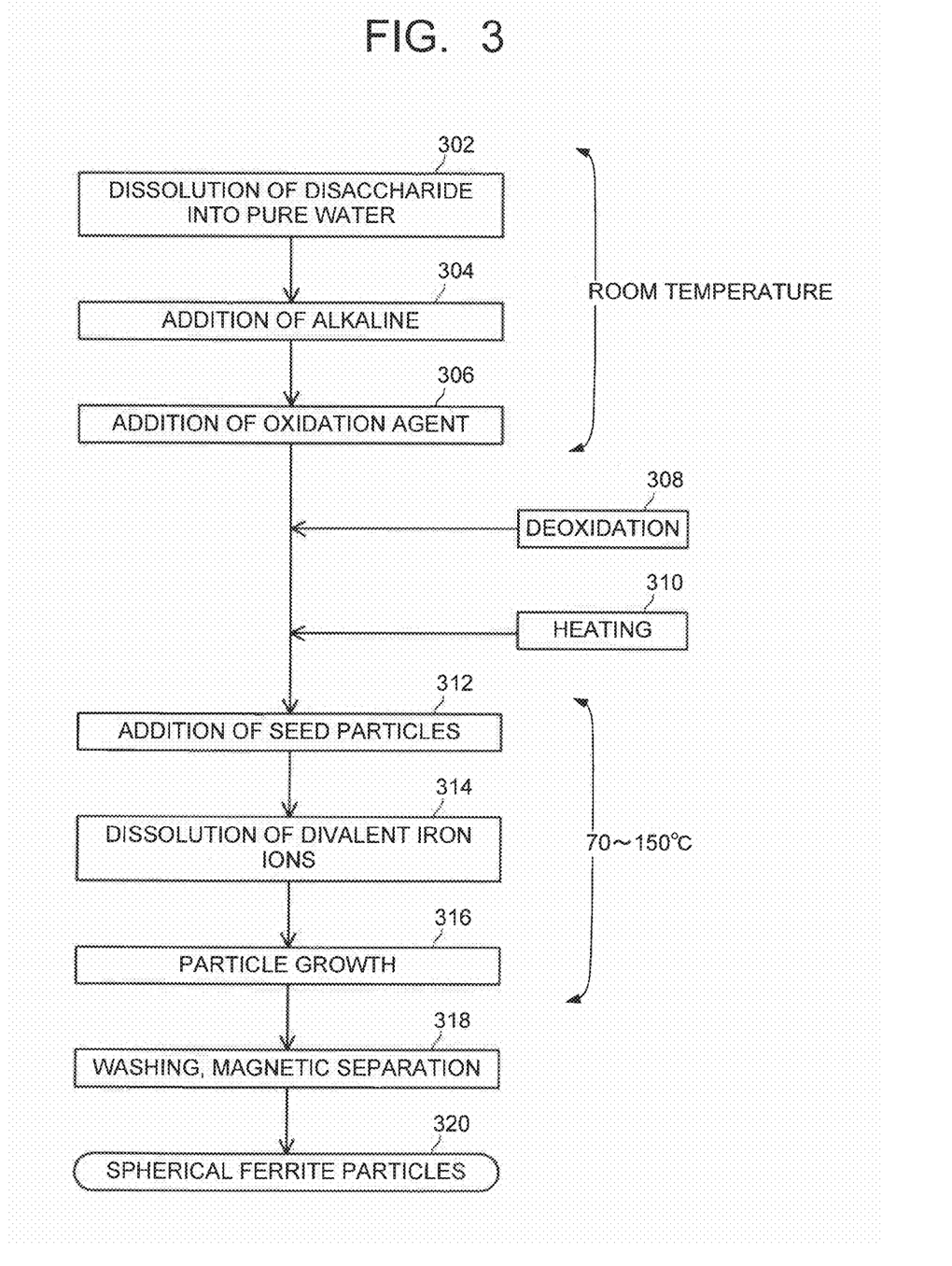
FIG. 3 is a flowchart showing the steps in the producing method according to still another embodiment of the present invention.

FIGS. 1 to 3 are flowcharts showing the steps in the producing methods according to the embodiments of the present invention, respectively. As shown in FIG. 1, a disaccharide is dissolved into an $O_2$-removed pure water at Step 102. The $O_2$-removed pure water can be prepared through the bubbling of $N_2$ gas so that oxygen can be sufficiently removed from the pure water. Then, a ferrous chloride or the like as a raw material of ferrite nanoparticles to be synthesized are added into the thus obtained solution so that the divalent iron ions from the ferrous chloride or the like can be added into the solution at Step 104. Then, minute seed particles are added into the solution at Step 106. As the minute seed particles, magnetite particles or the like with an average particle diameter of about 8 nm much smaller than the particle sizes of the ferrite nanoparticles to be synthesized may be employed. Then, an alkaline such as sodium hydroxide and potassium hydroxide is added into the solution in order to increase the pH value of the solution up to about 7 at Step 108. Steps 102 through 110 are preferably conducted at room temperature under the condition of the agitation of the solution. The pH value of the solution may be increased to about 9, for example.

Then, an oxidation agent such as a sodium nitrate is added into the solution at Step 110. Then, the thus obtained solution is introduced into a container so that particle growth can be conducted at Step 112. Since the particle growth rate of the ferrite nanoparticles becomes slow at low temperature, the particle growth temperature is preferably set to 4° C. or more, more preferably room temperature or more, particularly 50° C. or more. If the particle growth temperature is set to about 180° C. or more, the disaccharide may be decomposed. Therefore, the particle growth temperature is preferably set to 180° C. or less, more preferably 150° C. or less. The heating process can be conducted using an autoclave. Here, if the particle growth temperature is set to 100° C. or less, the synthesizing apparatus can be simplified because no moisture vapor with high pressure is generated. Then, washing and magnetic separation are conducted at Step 114 after the particle growth step to obtain the intended ferrite nanoparticles 116.

Here, as shown in FIG. 2, Step 106 for adding the seed particles may be set after Step 110 for adding the alkaline. Like or corresponding steps are designated by the same reference numerals through FIGS. 1 and 2.

Then, the process shown in FIG. 3 may be employed. In FIG. 3, a disaccharide is dissolved into a pure water at Step 302, and then, an alkaline is added into the thus obtained solution at Step 304. Then, an oxidation agent is added into the solution at Step 306. In this way, the solution containing the disaccharide, the alkaline and the oxidation agent can be obtained. The solution is deoxidized through the bubbling of an inactive gas such as an $N_2$ gas. Then, the heating treatment is conducted at Step 310 and the seed particles are added into the solution at Step 312. Then, the divalent iron ions are added into the solution at Step 314 and the particle growth is conducted at Step 316 to grow the spherical ferrite particles. In this case, if the $N_2$ gas continues to be supplied into the container, the inside of the container is not contaminated with oxygen. Therefore, the ferrite nanoparticle growth can be conducted in the same container so that the solution is not required to be transferred into an air-tight container. The thus grown spherical ferrite nanoparticles are washed and magnetically separated to obtain the intended spherical ferrite nanoparticles 320. That the spherically grown ferrite nanoparticles can be obtained without transferring the solution into another air-tight container is advantageous for producing the ferrite nanoparticles. In the case that the ferrite nanoparticles are produced on a small scale according to the producing method of the present invention, for example, the solution is input into an Erlenmeyer flask under the condition that the tubes for injecting an inactive gas for deoxidation and for adding an oxidation agent solution are provided at the plug for the flask and a through-hole for gas purging is also formed at the plug for the flask. Thereafter, the flask (solution) is heated at a hot plate. In this way, the ferrite nanoparticles can be produced on a small scale using some simple instruments. As a matter of course, the ferrite nanoparticles can be simply and easily produced on a large scale.

The surface-modified spherical ferrite nanoparticles according to the present invention can be obtained as follows. First of all, the spherical ferrite nanoparticles are input into a solution containing a surface-active agent and/or molecules such as hydroxyl acid and sugar alcohol, washed and magnetically collected. Here, the surface-active agent and the molecules are dissolved in the solution. As the surface-active agent, a fatty acid, an alkylbenzene sulfonic acid and an alkyl phosphoric acid may be employed. As the hydroxyl acid, a citric acid, a tartaric acid and a malic acid may be exemplified. As the sugar alcohol, a sorbitol and a xylitol may be exemplified. In this way, if the spherical ferrite nanoparticles are surface-modified, the dispersion of the spherical ferrite nanoparticles is enhanced. In this point of view, if the surface-modified ferrite nanoparticles are dispersed in a water, a ferrite nanoparticle-dispersed solution, where the ferrite nanoparticles are unlikely to be precipitated, can be obtained.

Example 1

Addition of Sucrose

A seed particles were employed under the existence of a disaccharide to produce ferrite nanoparticles. First of all, oxygen was sufficiently removed from a pure water through the bubbling of $N_2$ gas, and then, a sucrose was dissolved as the disaccharide into the pure water. Then, a ferrous chloride was dissolved into the thus obtained solution. Then, a sodium hydroxide solution and seed particles were subsequently added into the solution. Lastly, a sodium nitrate was added as an oxidation agent into the solution. The thus obtained solution was input into a heat and pressure-resistant container with air tight so that particle growth was conducted by means of hydrothermal technique. The solution was cooled down up to room temperature so that the ferrite nanoparticles grown in the solution were magnetically collected by means of magnets. The collected ferrite nanoparticles were dispersed in a pure water and then, magnetically collected again. Namely, the process of dispersing the ferrite nanoparticles into a pure water and magnetically collecting the ferrite nanoparticles dispersed in the pure water was repeated so as to wash the ferrite nanoparticles with pure waters. As a result, the intended ferrite nanoparticles were obtained.

Here, the contents (concentrations) of the components subsequently added into the pure water were set as follows. Moreover, the total amount of the solution was set to 40 mL and the hydrothermal treatment was conducted at 90° C. for three hours.

Figure 4A:
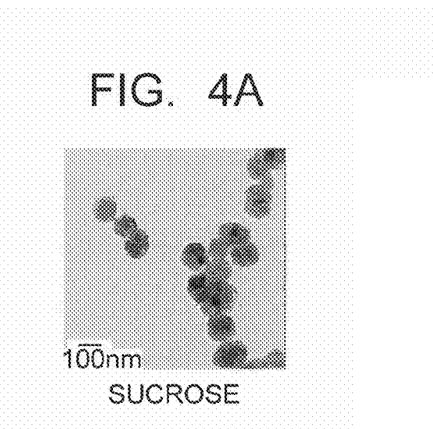
FIG. 4 relates to the transmission electron microscope photographs of the spherical ferrite nanoparticles obtained in Examples.

Ferrous chloride ($FeCl_2 \cdot 4H_2O$: Wako Pure Chemical Industries, Ltd) 0.075M Sodium hydroxide (NaOH: Wako Pure Chemical Industries, Ltd) 0.1M Sodium nitrate ($NaNO_3$: Wako Pure Chemical Industries, Ltd) 0.2M Seed particles (Magnetite particles made by means of coprecipitation, average particle size=8 nm) 2.7 mg/40 mL Disccharide: sucrose (Wako Pure Chemical Industries, Ltd) 0.5 M FIG. 4 shows the transmission electron microscope of the ferrite nanoparticles obtained in this Example with the ferrite nanoparticles obtained in other Examples. FIG. 4A corresponds to the transmission electron microscope photograph of the ferrite nanoparticles obtained by using the sucrose in this Example. As apparent from FIG. 4A, the particle sizes of the ferrite nanoparticles obtained in this Example were uniform entirely.

As the result of the X-ray diffraction analysis for the ferrite nanoparticles in this Example, it was turned out that the ferrite nanoparticles have a diffraction line originated from a single spinnel phase. It is considered that the spinnel phase containing Fe is made from at least one of magnetite, maghemite and intermediate thereof. Next, Moessbauer spectrum was examined for the ferrite nanoparticles so that the thus obtained Moessbauer spectrum was compared with the Moessbauer spectrum for the ferrite nanoparicles synthesized without the addition of sucrose. As a result, it was turned out that the ferrite nanoparticles obtained in this Example were made from magnetite and maghemite and in comparison with the ferrite nanoparticles synthesized without the addition of sucrose, has a small amount of $Fe^{2+}$ and a large amount of maghemite.

Example 2

Addition of Cellobiose

The sucrose in Example 1 was substituted with a cellobioise. The content (concentration) of the cellobiose was set to 0.25M and the content (concentration) of the sodium nitrate as the oxidation agent was increased to 1.0M from 0.2M because the cellobiose was a reducing disaccharide. Except the above-described conditions, the ferrite nanoparticles were produced in the same manner as in Example 1.

Figure 4B:
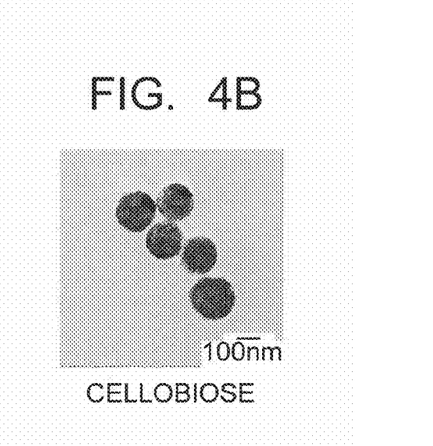

As a result, it was turned out that the thus obtained ferrite nanoparticles were spherical and have a uniform particle size under the condition that the amount of the seed particles in this Example was set equal to the one in Example 1, as shown in FIG. 4B. The particle sizes fell within a range of about 150 nm±13 nm.

Example 3

Addition of Maltose

The ferrite nanoparticles were produced in the same manner as in Example 2 except that the cellobiose was substituted with a maltose.

Figure 4C:
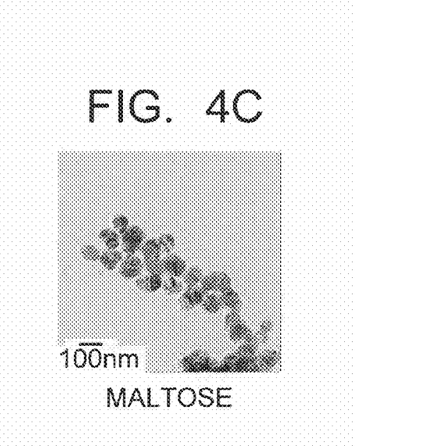

As a result, it was turned out that the thus obtained ferrite nanoparticles were spherical and have a uniform particle size under the condition that the amount of the seed particles was set equal to 2.7 mg/40 mL, as shown in FIG. 4C. The particle sizes fell within a range of about 70 nm±7 nm which is smaller than the particle size range of about 150 nm±13 nm in Example 2.

Example 4

Addition of Lactose

The ferrite nanoparticles were produced in the same manner as in Example 2 except that the cellobiose was substituted with a lactose.

Figure 4D:
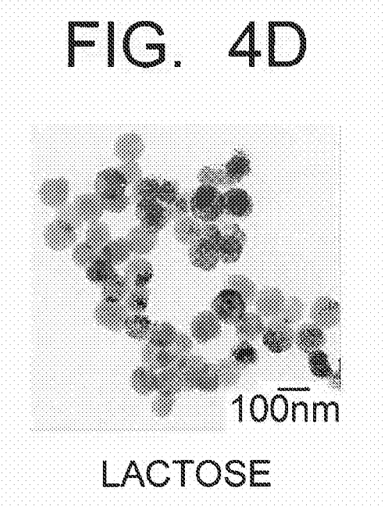

As a result, it was turned out that the thus obtained ferrite nanoparticles were spherical and have a uniform particle size so that the fluctuation in particle size of the ferrite nanoparticles is very small, as shown in FIG. 4D. The particle sizes fell within a range of about 90 nm±9 nm.

The particle images of 150 ferrite particles shown in the transmission electron microscope photograph in FIG. 4D, that is, synthesized in Example 4 were measured to obtain the particle size distribution. The measurement result was shown in Table 1. Referring to Table 1, it was turned out that the particle sizes of the 150 ferrite particles fell within a range of 55 nm±20 nm (herein, "55 nm" means a number-averaged particle size). According to the present invention, therefore, the particle size distribution can be narrowed so that the ferrite nanoparticles of 95% or more for all of the ferrite nanoparticles fall within a range of ±40% for the number-averaged particle size as standard.

TABLE 1

| SECTION (nm) | NUMBER | RATIO (%) |
| --- | --- | --- |
| 25 | 0 | 0 |
| 30 | 0 | 0 |
| 35 | 2 | 1.33 |
| 40 | 5 | 3.33 |
| 45 | 20 | 13.33 |
| 50 | 32 | 21.33 |
| 55 | 35 | 23.33 |
| 60 | 27 | 18 |
| 65 | 19 | 12.67 |
| 70 | 6 | 5.33 |
| 75 | 2 | 1.33 |
| 80 | 0 | 0 |
| 85 | 0 | 0 |
| 90 | 0 | 0 |

Moreover, the particle size distribution is matched with a normal distribution. On the other hand, it is known that the ferrite nanoparticles synthesized by a normal technique is not matched with a normal distribution, but with a logarithmic normal distribution.

Example 5

Addition of Trehalose

The sucrose in Example 1 was substituted with a trehalose. The content of the sodium nitrate as the oxidation agent was set to 0.2M and then, the ferrite nanoparticles were produced in the same manner as in Example 1. Here, the trehalose is a reducing disaccharide.

Figure 4E:
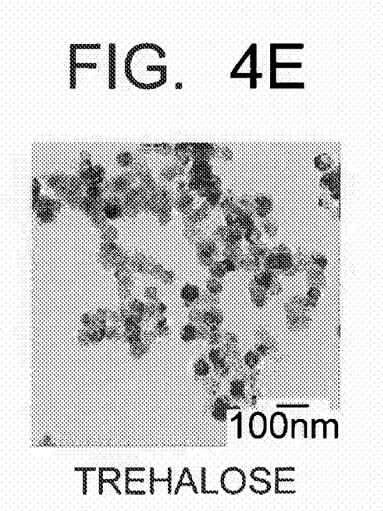
Figure 5:
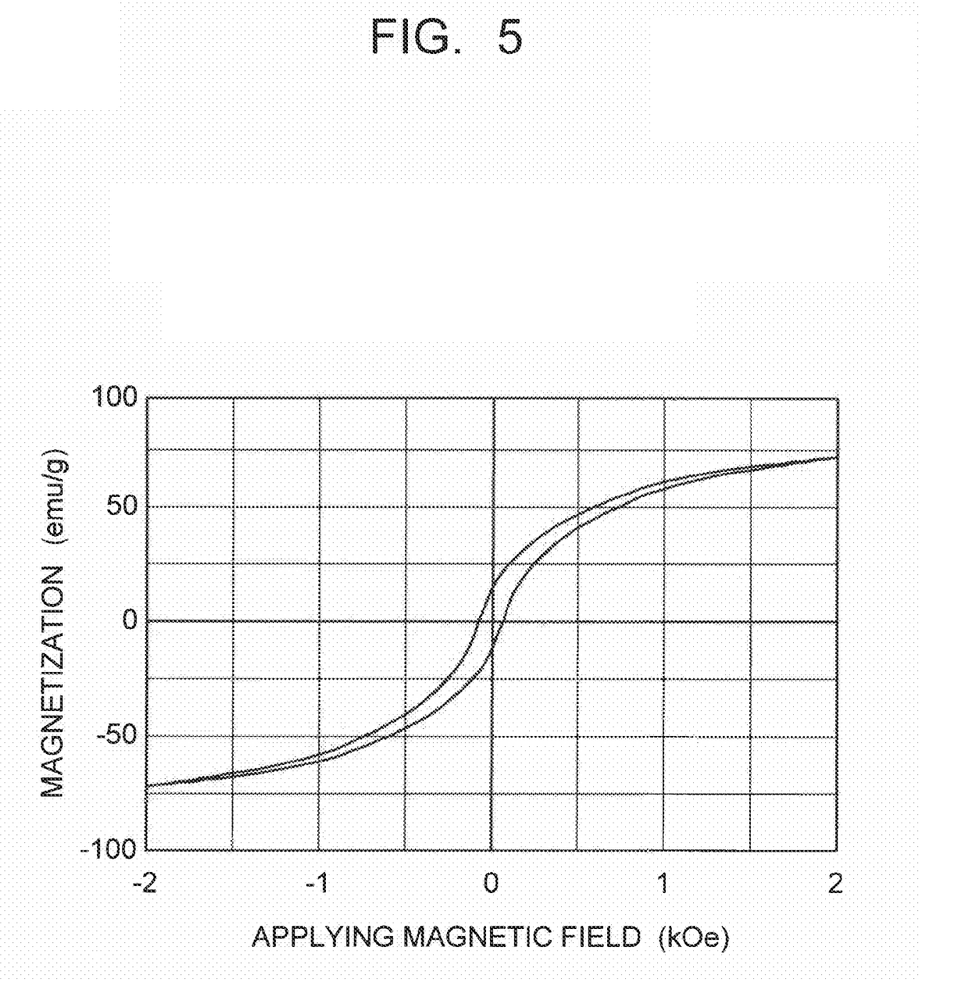
FIG. 5 is a graph showing the result in magnetization measurement of the ferrite nanoparticles according to an embodiment of the present invention.

As a result, the particle sizes fell within a range of about 50 nm±6 nm, as shown in FIG. 4E.

Example 6

Dependence on Amount of Seed Particles

Figure 6A:
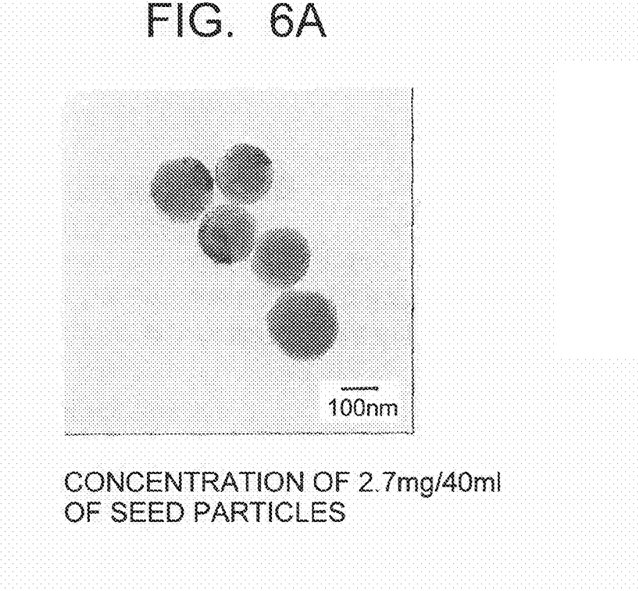
FIG. 6 relates to the transmission electron photographs of the ferrite nanoparticles obtained under the condition of "A" input of seed particles being set to 2.7 mg/40 mL and under the condition of "B" input of seed particles being set to 13.5 mg/40 mL.
Figure 6B:
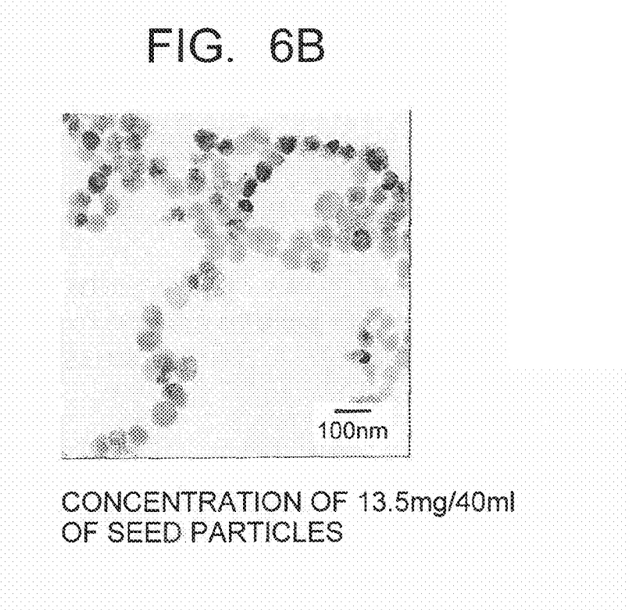

The ferrite nanoparticles were produced in the same manner as in Example 2 except that the amount of the seed particles is increased to 13.5 mg/40 mL from 2.7 mg/40 mL. As a result, the number of the ferrite nanoparticles obtained through synthesis was increased while the particle size can be decreased within a range of about 50 nm±6 nm. FIG. 6 shows the transmission electron microscope photographs of the ferrite nanoparticles. FIG. 6A shows the transmission electron microscope photograph of the ferrite nanoparticles under the condition that the amount of the seed particles is set to 2.7 mg/40 mL and FIG. 6B shows the transmission electron microscope photograph of the ferrite nanoparticles under the condition that the amount of the seed particles is set to 13.5 mg/40 mL. As apparent from FIG. 6, even though the amount of the seed particles is set to 13.5 mg/40 mL, the resultant ferrite nanoparticles are maintained spherical and in a uniform particle size.

Next, the ferrite nanoparticles were produced in the same manner as in Example 3 except that the amount of the seed particles is increased to 13.5 mg/40 mL from 2.7 mg/40 mL. As a result, the number of the ferrite nanoparticles obtained through synthesis was increased while the particle size can be decreased within a range of about 30 nm±4 nm. Even though the amount of the seed particles is set to 13.5 mg/40 mL, the resultant ferrite nanoparticles are maintained spherical and in a uniform particle size.

In view of these results, it was turned out that the ferrite nanoparticles can be made spherically and have a uniform particle size by controlling the amount of the seed particles.

Example 7

Dependence on Content (Concentration) of Disacchadise

The content (concentration) of the sucrose was increased to 0.75M and 1.0M from 0.5M in Example 1 so as to examine the effect on the resultant ferrite nanoparticles.

As a result, in the case that the content of the sucrose was increased to 0.75M, the particle sizes of the resultant ferrite nanoparticles were inclined to be increased. In the case that the content of the sucrose was increased to 1.0M, the surfaces of the resultant ferrite nanoparticles were inclined to be roughed.

Example 8

Dependence on Heating Temperature and Heating Period of Time

The ferrite nanoparticles were produced in the same manner as in Example 1 except that the heating temperature was varied within a range of 50° C. to 150° C. and the heating period of time was varied within a range of 1 hour to 24 hours so as to examine the effect on the resultant ferrite nanoparticles.

As a result, it was turned out that the heating period of time does not affect the particle sizes and shapes of the resultant ferrite nanopaticles irrespective of the heating temperature within the above-defined temperature range. In this point of view, it is considered the synthesis for producing the ferrite nanoparticles is terminated.

On the other hand, it was turned out that the particle sizes of the ferrite nanoparticles were within a range of 80 nm to 100 nm at a heating temperature within a range of 50° C. to 150° C. while the ferrite nanoparticles are made spherically and have a uniform particle size.

Example 9

Addition of Trivalent Iron Ions

The ferrite nanoparticles were produced in the same manner as in Example 1 except that a small amount of ferric chloride was added so as to examine the effect on the resultant ferrite nanoparticles.

As a result, the intended spherical ferrite nanoparticles were produced under the condition of $Fe^{3+}/Fe^{2+}=0.1$. On the other hand, the particle sizes of the ferrite nanoparticles were decreased under the condition that the content of $Fe^{3+}$ ions is larger than the content of $Fe^{2+}$ ions, that is, the condition of $Fe^{3+}/Fe^{2+}=0.5$ or 0.25, which is originated from that the $Fe^{3+}$ ions may allow the nucleation remarkably.

Example 10

Oxygen was sufficiently removed from the first aqueous solution containing the sucrose, the sodium hydroxide and the sodium nitrate through the bubbling of $N_2$ gas, and the aqueous solution was heated at 90° C. Thereafter, the second aqueous solution containing the seed particles and ferrous chloride was prepared and added into the first aqueous solution. The thus obtained third aqueous solution was agitated with kept at 90° C. and supplying $N_2$ gas to conduct particle growth. After three hours elapsed, the third aqueous solution was cooled down, and the grown ferrite nanoparticles were magnetically collected and washed with a pure water. The contents of the compositions to be employed were set equal to the ones in Example 1. As a result, the particle sizes of the spherical ferrite nanoparicles fell within a range of 146 nm±11 nm.

Example 11

The ferrite nanoparticles were produced in the same manner as in Example 10 except that the sodium hydroxide was substituted with a tetramethyl ammonium hydroxide. As a result, the particle sizes of the spherical ferrite nanoparticles fell within a range of 100 nm±15 nm.

Example 12

The spherical ferrite nanoparticles with a particle size of about 100 nm was input into a sodium citrate aqueous solution with a concentration of 100 mM, and agitated for one hour. Then, washing and magnetic collection were conducted to obtain the ferrite nanoparticles modified in surface with the citric acid. The surface-modified spherical ferrite nanoparticles were dispersed in a pure water for three days, but not precipitated.

Comparative Example 1

No Seed Particle

The ferrite nanoparticles were produced in the same manner as in Example 1 except that the seed particles were not added so as to examine the effect on the resultant ferrite nanoparticles. Moreover, the content of the sucrose was varied from 0.5M so as to examine the effect on the resultant ferrite nanoparticles.

As a result, it was observed that under the condition that the seed particles were not added, the ratio of the spherical ferrite nanoparticles to all of the ferrite nanoparticles was increased as the content (concentration) of the sucrose was increased to 0.25M from 0.15M and to 0.5M from 0.25M. However, the ferrite nanoparticles have the respective various shapes as a whole so that the particle size distribution was enlarged. Moreover, it was turned out that no ferrite particle was produced when the content (concentration) of the sucrose is beyond 0.5M.

Comparative Example 2

Addition of Monosaccharide

The ferrite nanoparticles were produced in the same manner as in Example 1 except that the sucrose as a disaccharide was substituted with a glucose as a monosaccharide. In this case, the content (concentration) of the glucose was set to 0.25M. Since the glucose is a reducing saccharide, the content (concentration) of the oxidation agent was increased to 1.0M.

As a result, it was turned out that the resultant ferrite nanoparticles were made spherical even though the glucose was added. When the content of the seed particles was increased to 13.5 mg/40 mL from 2.7 mg/40 mL, the seed particles were not almost grown and thus remained the same. When the content (concentration) of the glucose was increased to 0.5M from 0.25M, the surfaces of the ferrite nanoparticles were roughed and thus not made spherical. When the content (concentration) of the glucose was beyond 0.5M, green rusts were produced so that no ferrite nanoparticle was produced. In this way, the coexistence of the glucose causes the enlargement of the particle size distribution even though the seed particles were employed.

In addition, such an attempt as producing the ferrite nanoparticles under the condition that a fructose, a galactose or a mannose was added as another monosaccharide was made. In each case, however, only green rusts were produced while no ferrite nanoparticle was produced.

Comparative Example 3

Addition of Polysaccharide with Three or More Monosaccharides

The ferrite nanoparticles were produced in the same manner as in Example 1 except that the sucrose as a disaccharide was substituted with a dextran with a molecular weight of 60,000 to 90,000 or with a molecular weight of 90,000 to 210,000.

As a result, it was turned out that the resultant ferrite nanoparticles were made spherical even though the dextran was added. However, the particle size distribution became large. The particle sizes, shapes and particle size distribution of the ferrite nanoparticles do not depend on the molecular weight of the dextran.

INDUSTRIAL APPLICABILITY

Since the ferrite nanoparticles produced according to the present invention are shaped spherically so as not to have plane surfaces, and have a uniform particle size, the ferrite nanoparticles can be easily separated from one another and thus passed through a minute flow path while the dispersion of the ferrite nanoparticles is excellent. Therefore, the ferrite nanoparticles are suitable for MEMS and the like in addition to various biochemical applications and medical care applications. In this point of view, industrial applicability is much expected for the producing method of the spherical ferrite nanoparticles and the spherical ferrite nanoparticles produced by the producing method.

What is claimed is:

1. A method for producing spherical ferrite nanoparticles, comprising:
    preparing a first aqueous solution comprising a disaccharide, an alkaline, an oxidation agent, ferrite seed particles and divalent iron ions; and
    conducting particle growth in said first aqueous solution to produce the spherical ferrite nanoparticles.

2. The method as set forth in claim 1,
    wherein said first aqueous solution is prepared by adding the ferrite seed particles and the divalent iron ions
    to a second aqueous solution comprising the disaccharide, the alkaline and the oxidation agent.

3. The method as set forth in claim 1,
    wherein said first aqueous solution is prepared by adding the alkaline and the ferrite seed particles to a third aqueous solution comprising the divalent iron ions and the disaccharide to form a fourth aqueous solution and adding the oxidation agent to said fourth aqueous solution.

4. The method as set forth in claim 1, further comprising adding trivalent iron ions to the first aqueous solution.

5. The method as set forth in claim 1,
    wherein a concentration of the disaccharide in the first aqueous solution is set within a range of 0.1M to 5M; and
    wherein a ratio of the concentration of the divalent iron ions to the concentration of the disaccharide is set within a range of 0.002 to 50.

6. The method as set forth in claim 1,
    wherein the oxidation agent is at least one selected from the group consisting of nitric acid, nitrous acid, a nitrate and a nitrite.

* * * * *